(12) United States Patent
Valpey, III et al.

(10) Patent No.: US 8,440,171 B2
(45) Date of Patent: *May 14, 2013

(54) COMPOSITION AND ITS PHYSICAL REQUIREMENTS FOR ELIMINATING ODORS IN AIR

(75) Inventors: Richard S. Valpey, III, Lindenhurst, IL (US); Paul A. Clark, Racine, WI (US); Maciej K. Tasz, Racine, WI (US); Peter N. Nguyen, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1210 days.

This patent is subject to a terminal disclaimer.

(21) Appl. No.: 11/476,243

(22) Filed: Jun. 28, 2006

(65) Prior Publication Data

US 2006/0292111 A1 Dec. 28, 2006

Related U.S. Application Data

(60) Provisional application No. 60/694,439, filed on Jun. 28, 2005.

(51) Int. Cl.
*A61K 9/12* (2006.01)
*A61K 8/02* (2006.01)
*A01N 25/00* (2006.01)
*A01N 25/02* (2006.01)

(52) U.S. Cl.
USPC ............. 424/45; 424/401; 424/404; 424/405

(58) Field of Classification Search .................... 424/45, 424/401, 404, 405
See application file for complete search history.

(56) References Cited

U.S. PATENT DOCUMENTS

| | | | |
|---|---|---|---|
| 2,757,278 A | 7/1956 | Cloud | |
| 2,964,165 A | 12/1960 | Riley | |
| 3,131,153 A | 4/1964 | Klausner | |
| 3,160,555 A | 12/1964 | Hamill et al. | |
| 3,787,566 A | 1/1974 | Gauvreau | |
| 3,821,413 A | 6/1974 | Hellyer, Jr. | |
| 4,294,821 A | 10/1981 | Neumiller | |
| 4,350,605 A * | 9/1982 | Hughett | ............................ 516/7 |
| 4,748,279 A | 5/1988 | Whiteley | |
| 5,091,111 A | 2/1992 | Neumiller | |
| 5,356,479 A | 10/1994 | Menke et al. | |
| 5,591,395 A | 1/1997 | Schroeder et al. | |
| 5,702,631 A * | 12/1997 | Conville et al. | ................... 252/76 |
| 5,773,016 A * | 6/1998 | Nelson | ........................... 424/405 |
| 6,395,236 B1 | 5/2002 | Stewart | |
| 6,569,387 B1 | 5/2003 | Furner et al. | |
| 6,610,254 B1 | 8/2003 | Furner et al. | |
| 7,307,053 B2 * | 12/2007 | Tasz et al. | ...................... 510/384 |
| 2003/0145965 A1 | 8/2003 | Anderson et al. | |
| 2004/0026462 A1 | 2/2004 | Moshontz et al. | |
| 2004/0144864 A1 | 7/2004 | Valpey, III et al. | |
| 2007/0194040 A1 * | 8/2007 | Tasz et al. | ........................... 222/4 |
| 2008/0003185 A1 * | 1/2008 | Valpey et al. | .................... 424/43 |

FOREIGN PATENT DOCUMENTS

| | | |
|---|---|---|
| EP | 0420538 A1 | 4/1991 |
| GB | 998776 | 7/1965 |
| WO | WO 00/54585 | 9/2000 |
| WO | WO 2006/102052 A2 | 9/2006 |

OTHER PUBLICATIONS

The Merck Index, 10th edition, Merck & Co., Inc.: Rahway, NY, 1983, pp. 10 (acetone: entry 58), pp. 34-35 (alcohol, anhydrous: entry 212), and pp. 749 (isopropyl alcohol: entry 5057).*
"HLB Systems", accessed on Jun. 11, 2012 at pharmcal.tripod.com/ch17.htm.*
The Encyclopedia of Chemistry, 3rd edition, Clifford A. Hampel and Gessner G. Hawley, eds., Van Nostrand Reinhold Co.: New York, 1973, pp. 38-39.*

* cited by examiner

*Primary Examiner* — James H. Alstrum-Acevedo

(57) ABSTRACT

An air treating composition for eliminating odors from air in combination with specific spray valve and actuator requirements and spray performance parameters providing maximum dispersion of the active component in the composition into the air is disclosed. The particles of the composition are small so that the active component is dispersed into air as a fine dispersion to provide more contact with odors and to provide quick absorption of odors. The particle size of the composition is controlled through the selection of valve and actuator dimensions. The air treating and odor eliminating composition of the invention includes water, a low molecular weight polyol, an emulsifier, and a propellant. The composition may also include additional adjuvants such as solvent(s), fragrance(s), corrosion inhibitor, pH adjustor and the like.

13 Claims, 3 Drawing Sheets

US 8,440,171 B2

COMPOSITION AND ITS PHYSICAL REQUIREMENTS FOR ELIMINATING ODORS IN AIR

CROSS REFERENCE TO RELATED APPLICATION

This application is related to, and claims the priority benefit of, U.S. Provisional Patent Application No. 60/694,439, filed Jun. 28, 2005.

FIELD OF INVENTION

The invention is directed to an air treating, in particular an odor eliminating, composition in combination with specific spray valve requirements and spray performance parameters to provide maximum dispersion of the active component in the composition into the air. Specifically, the particles of the composition are small so that the active component is dispersed into the air as a fine dispersion to provide good contact with odors and to provide quick absorption of odors. The particle size is controlled through the selection of valve and actuator dimensions along with formulation requirements including propellant contents of 25% or less.

BACKGROUND OF THE INVENTION

Various compositions are available to mask odors in the air. Additionally, various compositions are available to sanitize and remove odors from the air. These compositions may be dispensed by various spray devices including aerosol dispensers.

Aerosol dispensers have been commonly used to dispense personal, household, industrial, and medical products, and to provide a low cost, easy to use method of dispensing a liquid product. Typically, aerosol dispensers include a container, which contains a liquid product to be dispensed, such as sanitizer, soap, insecticide, deodorant, or the like. A propellant is used to discharge the liquid product from the container. The propellant is under pressure and provides a force to expel the liquid product from the container when a user actuates the aerosol dispenser by, for example, pressing an actuator button.

A conventional aerosol dispenser generally comprises a container (not shown) for holding a liquid product and a propellant, and a valve assembly for selectively dispensing a liquid product from the container. As illustrated in FIG. 3, the valve assembly 104 comprises a mounting cup 106, a mounting gasket 108, a valve body 110, a valve stem 112, a stem gasket 114, an actuator cap 116, and a return spring 118. The valve stem 112, stem gasket 114, and return spring 118 are disposed within the valve body 110 and are movable relative to the valve body 110 to selectively control dispensing of the liquid product. The valve body 110 is affixed to the underside of the mounting cup 106, such that the valve stem 112 extends through, and projects outwardly from, the mounting cup 106. The actuator cap 116 is fitted onto the outwardly projecting portion of the valve stem 112 and is provided with an actuator orifice 132. The actuator orifice 132 directs the spray of the liquid product into the desired spray pattern. A dip tube 120 is attached to the lower portion of the valve body 110 to supply the liquid product to the valve assembly 104 to be dispensed. The whole valve assembly 104 is sealed to a container by the mounting gasket 108.

In operation, when the actuator cap 116 of a dispenser is depressed, the propellant forces the liquid product up the dip tube 120 and into the valve body 110 via a body orifice 122.

In the valve body 110, the liquid product may be mixed with additional propellant supplied to the valve body 110 through a vapor tap 124. The vapor tap 124 helps to mix the liquid product and propellant in the valve body 110, to thereby break up the product into smaller particles suitable to be dispensed. From the valve body 110, the product is propelled through a stem orifice 126, out the valve stem 112, and through an actuator orifice 132 formed in the actuator cap 116.

S.C. Johnson & Son, Inc. (S.C. Johnson) employs an aerosol valve similar to that shown in FIG. 3 in connection with their line of Oust® air sanitizers. The propellant used to propel the air sanitizer liquid product from the container may be a B-Series propellant having a propellant pressure of 40 psig (B-40), at 70° F. (2.722 atm at 294.261 K). "Propellant pressure" refers to the approximate vapor pressure of the propellant, as opposed to "can pressure," which refers to the initial gauge pressure contained within a full aerosol container. The B-40 propellant is a composition of propane, normal butane, and isobutane. By normal butane, it is meant the composition denoted by the chemical formula $C_4H_{10}$, having a linear backbone of carbon. In order to effectively dispense this air sanitizer composition, the aerosol dispenser used by S.C. Johnson in connection with their line of Oust® air sanitizers has a stem orifice diameter of 2×0.020" (2×0.508 mm), i.e., two holes of 0.020" diameter, a vapor tap diameter of 0.020" (0.508 mm), a body orifice diameter of 0.062" (1.575 mm), and a dip tube inner diameter of 0.060" (1.524 mm). Currently known aerosol air sanitizers contain hydrocarbon propellant in the amount of approximately 29.5% by weight of the contents of the dispenser assembly along with 6-8.8% glycol levels and pure alcohol solvent.

Hydrocarbon propellants are considered to be Volatile Organic Compounds (VOCs). The content of VOCs in aerosol air sanitizers has the potential to be regulated by federal and/or state regulatory agencies, such as the Environmental Protection Agency (EPA) and California Air Resource Board (CARB). S.C. Johnson continuously strives to provide environmentally friendly products and regularly produces products that exceed government regulatory standards.

One way to reduce the VOC content in such aerosol air sanitizers is to reduce the content of the hydrocarbon propellant used to dispense the liquid product. However, a reduction in the propellant content can adversely affect the product performance. Specifically, reducing the propellant content in the aerosol air sanitizer may result in excessive product remaining in the container at the end of the life of the dispenser assembly (product retention) and an increase in the size of particles of the dispensed product (increased particle size). It is desirable to minimize the particle size of a dispensed product in order to maximize the dispersion of the particles in the air and to prevent the particles from "raining" or "falling out" of the air. Thus, an aerosol dispenser assembly that can satisfactorily dispense an aerosol product that comprises, at most, 25% by weight, of a hydrocarbon propellant, while providing high quality product performance throughout the life of the dispenser assembly is desired.

The "life of the dispenser assembly" is defined in terms of the pressure within the container (i.e., the can pressure), such that the life of the dispenser assembly is the period between when the pressure in the container is at its initial pressure (typically a maximum) and when the pressure within the container is substantially depleted, i.e., equal to atmospheric pressure.

One known method of reducing the particle size of a dispensed liquid product is disclosed in U.S. Pat. No. 3,583,642 to Crowell et al. (the '642 patent), which is incorporated herein by reference. The '642 patent discloses a spray head that incorporates a "breakup bar" for inducing turbulence in a product/propellant mixture prior to the mixture being discharged from the spray head. Such turbulence contributes to reducing the size of the mixture particles discharged from the spray head.

Also known is U.S. Pat. No. 3,160,555 which discloses an aerial disinfectant containing at least one polyhydroxy compound selected from a group including triethylene glycol (TEG), and at least one α-hydroxy carboxylic acid. TEG is disclosed as used as a bactericide in the disinfectant spray. The disinfectant can be a self-propelled pressurized aerosol spray.

Also known is U.S. Pat. No. 2,757,278 which discloses a combination ozone lamp and a vaporizer as a sanitary device. The '278 patent discloses that TEG is known for controlling odors, germs and bacteria. Vaporizers used therewith generally are operated by a resistance heater, such as an incandescent lamp.

Also known is U.S. Pat. No. 6,395,236 B1 which discloses a non-aerosol non-wick pump spray system consisting of an emulsion of TEG, surfactant, fragrance and distilled water. The system neutralizes tobacco smoke and sterilizes air of any airborne bacteria. Certain glycols, e.g. TEG, are capable of reacting with airborne bacteria. TEG is stated to be known to link with airborne tobacco smoke-based odors. TEG is disclosed for use in an amount of 0.5-6%. An aqueous TEG formula is also disclosed as an effective tobacco smoke odor neutralizer.

Also known is U.S. Pat. No. 3,787,566 which discloses disinfecting aerosol compositions including pyridinium halide salts admixed with a terpene to provide bacteriostatic activity. At column 5, lines 41-45, additives are disclosed which include TEG to provide additional disinfectant qualities and to control the humectant and degree of drying.

Also known is U.S. Patent Application Publication No. 2004/0026462 A1 which discloses an aerosol oxygenated air freshener including about 40 vol % compressed ambient air and a liquid component. The liquid component includes 50-90% water, 0.1-5% fragrance, 0.1-2% sodium nitrate, 0.5-5% TEG, and 5-50% propellant. Optional components include a solvent, anti-corrosive agent, surfactants, and mixtures thereof. TEG is stated to be present as an anti-corrosive agent. Example 1 at page 2 discloses an aerosol spray composition containing deionized water, TEG, sodium nitrate, SPAN 85 (sodium trioleate), ARLACEL C (sorbitan sesquioleate), ethanol, fragrance and a hydrocarbon blend.

Also known is U.S. Pat. No. 5,356,479 which discloses foam cleaners useful on hard surfaces. An example of a foam cleaner set forth in column 6, Table 1, Example 9 is stated to be a commercially available foam cleaner including C9-11 oxoalcohol 8EO, TEG, sodium citrate, water, fragrance and corrosion inhibitor.

Also known is International Published Application No. WO 00/54585 which discloses a germicidal composition for disinfecting or exterminating microorganisms which cause unpleasant odors and mildew. The composition includes a quaternary ammonium fungicide, a triazine bactericide and a volatile diluent which is an alcohol or a mixture of alcohol and water. Optional ingredients disclosed include TEG. The purpose of the TEG is not disclosed. The composition is dispensed by spraying.

Also known is U.S. Pat. No. 3,821,413 which discloses an aerial disinfectant for use in an air circulator to continuously reduce airborne bacteria in the surrounding atmosphere. Germicidal concentrations of glycol vapor are known to be odorless, tasteless, non-irritating, non-toxic, invisible and to have no deleterious effect on walls, fabrics, books or other objects in a treated space. The disinfectant composition includes the three essential components of (1) at least one glycol, (2) an organic polar coupling compound for maintaining homogeneity of the composition to prevent the glycol from separating out, and (3) an organic relatively non-polar compound for forming hydrophobic micelles with glycol molecules to reduce affinity of the glycol to atmospheric moisture, and thus increasing the rate of evaporation. The glycol component can be TEG.

Also known is U.S. Pat. No. 4,748,279 which discloses a liquid sterilizing composition including the reaction product of a non-ionic surfactant, a gluteraldehyde and TEG.

Also known is U.S. Patent Application Publication No. 2003/0145965 A1 which discloses a method of reducing undesirable odors generated in paper hand towels upon wetting involving the topical application of TEG, polyethylene glycol, a glycerol compound or mixtures thereof to a partially dewatered tissue web formed during a manufacturing process. Topical application can be by spraying.

SUMMARY OF THE INVENTION

The invention is directed to an air treating, in particular an odor eliminating, composition in combination with specific spray valve and actuator requirements and spray performance parameters to provide maximum dispersion of the active component in the composition into the air. Specifically, the particles of the composition are small so that the active component is dispersed into air as a fine dispersion to provide good contact with odors and to provide quick absorption of odors. The particle size of the composition is controlled through the selection of valve and actuator dimensions along with formulation requirements.

The composition of the invention is directed to an aerosol air treating composition comprising at least one low molecular weight polyol, i.e., a polyol having a molecular weight of about 250 g/mole or less. Preferred low molecular weight polyols are mono-, di- or tri-alkylene glycols or glycerol. A most preferred polyol is triethylene glycol (TEG) used alone or with propylene glycol. Aqueous solutions of polyols are difficult to effectively dispense in aerosol form since the solution is present in two phases and the polyol component participates in the emulsion. Trigger sprays are also generally not efficient since the particle size can not be sufficiently controlled due to the homogeneity of the mixture preventing the separation of the polyol therefrom during evaporation. The invention provides for a two-phase oil-out emulsion in a pressurized aerosol suitable for dispensing the aqueous polyol solution as a fine mist. The particle size of the invention is controlled through the selection of valve and actuator dimensions as well as formulation requirements.

The air treating composition of the invention comprises: water, a low molecular weight (MW) polyol, an emulsifier, and a propellant as follows:

| Ingredient | Wt. % |
|---|---|
| Water (Deionized) | 20–90 |
| Low MW Polyol (e.g. TEG) | 5–25 |
| Emulsifier (e.g., Sorbitan Monooleate) | 0.4–4 |
| Hydrocarbon Propellant | 10–25 |
| | 100.0 |

Adjuvants may also be present in the composition, for example, a solvent(s) which is preferably a low molecular weight alcohol such as for example ethanol and isopropanol, or acetone. When no solvent is present, an emulsifier is present as set forth above. If a solvent is present in the composition in an amount sufficient to form an emulsion, an emulsifier is not required and, thus, the emulsifier can be present in such instance in an amount of 0-4 wt. %. Additional adjuvants, such as fragrances, corrosion inhibitors, pH adjustors, antimicrobials, preservatives, and the like, are also suitable for inclusion. Preferred ranges for individual additional adjuvant compounds are from 0-about 5 wt. %, more preferably from 0-about 2 wt. %. A preferred pH of the composition is in a range of about 8 to about 10.

The above air treating composition may be used in combination with valve and actuator dimensions and spray performance parameters as follows:

| Dimension/Property | Range |
| --- | --- |
| Dip Tube Inner Diameter | 0.040"–0.060" |
| Vapor Tap Diameter | 0.003"–0.020" |
| Body Orifice Diameter | 0.008"–0.062" |
| Stem Orifice | 0.014"–0.030" |
| Particle Size (initial) | ≦45 micron |
| Particle Size (200 g) | ≦45 micron |
| Spray Rate | 0.5–2.5 g/sec |
| Retention | <5% |

Valve and actuator dimensions and spray performance parameters other than those above may also be present. As to the particle size, a more preferred particle size is in a range of about 25 to about 40 microns, and most preferably in a range of about 30 to about 38 microns.

The dispenser of the invention provides the desired small particle size and consistency throughout the life of the package. The retention rate obtained is also preferred. Procedures for determining particle size, spray rate and retention are described below.

The invention provides an aerosol dispenser assembly that dispenses substantially all of an aqueous air treating product (i.e., provides a low product retention) as a spray having a fine particle size and reasonable delivery rate, while at the same time employing a minimized amount of propellant to dispense the aqueous product from the container.

In one aspect, an aerosol dispenser assembly of the invention comprises a container that has an aqueous air treating product and a propellant for propelling the aqueous product from the container. The propellant is a hydrocarbon propellant and constitutes at most about 25% by weight of the contents of the container, more preferably about 20% by weight. The contents of the container are pressurized to between about 55 psig (3.743 atm) and about 120 psig (8.166 atm). In particular, the contents of the container are pressurized to between about 55 psig (3.743 atm) and about 80 psig (5.444 atm).

A valve attaches to the container for selectively dispensing the liquid product from the container as a mist, the mist having an average particle size of less than or equal to 45 µm (0.0018"), over at least the first 75% of the life of the dispenser assembly. Average particle size, as used herein, means mass median particle size (also known as the volumetric median) D(V,0.5) of the dispensed product, as measured by a Malvern® Mastersizer 2600 Particle Size Analyzer and as described in *Basic Principles of Particle Size Analysis*, by Dr. Alan Rawle, Malvern Instruments Limited. In addition, the dispenser assembly is capable of dispensing over 95% by weight of the aqueous polyol solution from the container, i.e., having less than 5% product retention, more preferably 98% by weight of the aqueous air treating product from the container, i.e., having less than 2% product retention.

A vapor tap is formed in the valve to facilitate thorough mixing of the propellant and the liquid product prior to dispensing, and a valve stem is disposed in the valve. The valve stem defines at least one stem orifice for flow of the combined product (i.e., the vapor from the vapor tap and liquid from the dip tube) during dispensing. The vapor tap has a diameter of about 0.003" (0.076 mm) to about 0.020" (0.508 mm), more preferably of about 0.013" (0.330 mm) to about 0.019" (0.483 mm) for dispensing in the 20-25% propellant range, and of about 0.003" (0.076 mm) to about 0.013" (0.330 mm) range for dispensing in the 15-20% propellant range.

A dispenser cap is mounted on the valve stem for actuating the valve to dispense the liquid product. The dispenser cap defines an exit path, through which the liquid product can be dispensed. An agitating/mixing component can be positioned in the exit path of the dispenser cap to break up or mix the liquid product in order to reduce the size of the particles before the liquid product is dispensed. The agitating/mixing component may be a spin chamber, a breakup bar, a stem tortuosity which is bent with a breakup geometry or any other suitable component.

The valve may also have specifications as described in U.S. Pat. Nos. 6,824,079 B2 and 7,014,127 B2 which are incorporated by reference herein.

A better understanding of these and other aspects, features, and advantages of the invention may be had by reference to the drawings and to the accompanying description, in which preferred embodiments of the invention are illustrated and described.

BRIEF DESCRIPTION OF THE DRAWINGS

Referring to the drawings.

Throughout the figures, like or corresponding reference numerals denote like or corresponding parts.

DETAILED DESCRIPTION OF THE INVENTION

The invention is directed to an air treating, in particular an odor eliminating, composition in combination with specific spray valve and actuator requirements and spray performance parameters to provide maximum dispersion of the active component in the composition into the air. Specifically, the particles of the composition are small so that the active component is dispersed into air as a fine dispersion to provide more contact with odors and quick absorption of the odors. The particle size of the composition is controlled through the selection of valve and actuator dimensions along with formulation requirements, e.g., propellant level and type, and formation of an oil-out emulsion upon shaking.

The composition of the invention is directed to an aerosol air treating composition comprising water, at least one low molecular weight (MW) polyol, an emulsifier, a propellant, and optionally a solvent. Low MW polyols suitable for use have a MW of about 250 grams/mole or less. Preferred examples of low MW polyols for use are mono- di- or tri-alkylene glycols, and glycerol. The alkylene is preferably ethylene or propylene. The most preferred low MW polyol for use is triethylene glycol (TEG). One or more low MW polyols may be used in the air treating composition, e.g. triethylene glycol with propylene glycol. The air treating composition of the invention may also comprise additional optional adjuvants such as fragrance(s), corrosion inhibitor(s), pH adjustor(s), antimicrobial(s), preservative(s) and the like. An individual additional adjuvant compound is generally present in an amount of 0-about 5 wt. %. The components of the composition are preferably present as follows:

| Ingredient | Wt. % |
|---|---|
| Water (Deionized) | 20–90 |
| Low MW Polyol(s) (e.g. TEG) | 5–25 |
| Emulsifier (e.g., Sorbitan Monooleate) | 0.4–4 |
| Propellant (Hydrocarbon) | 10–25 |
| Solvent (e.g., ethanol) | 0–60 |
| Fragrance | 0–5 |
| Corrosion Inhibitor (e.g., MonoSodium Phosphate) | 0–2 |
| pH adjustor (e.g., NaCH) | 0–2 |
| | 100 |

The solvent is preferably a high vapor pressure alcohol, such as for example ethanol and isopropanol, or acetone. The preferred solvent is ethanol. In preferred embodiments, no solvent is present and, thus, an emulsifier is required to be present as set forth above to insure formation of an emulsion. However, if a solvent is present in an amount sufficient to form an emulsion, the emulsifier can be present in an amount in a range of 0-4 wt. %. A preferred amount of solvent, suitable for use in both the presence and absence of an emulsifier is from about 25 to about 45 wt. %, more preferably from about 30 to about 40 wt. %.

Figure 2:
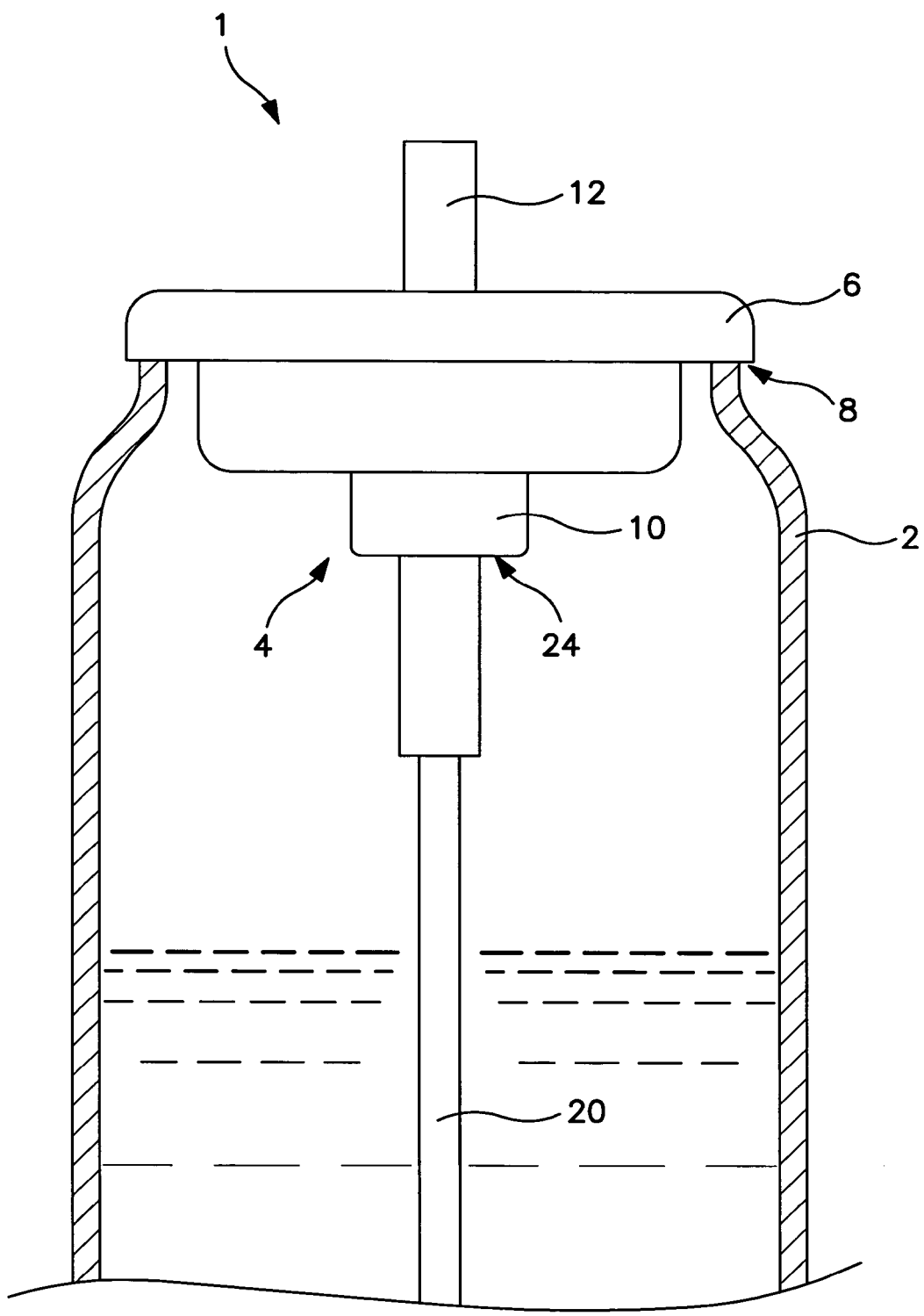
FIG. 2 is a front view of the aerosol dispenser assembly for the valve of FIG. 1.
Figure 3:
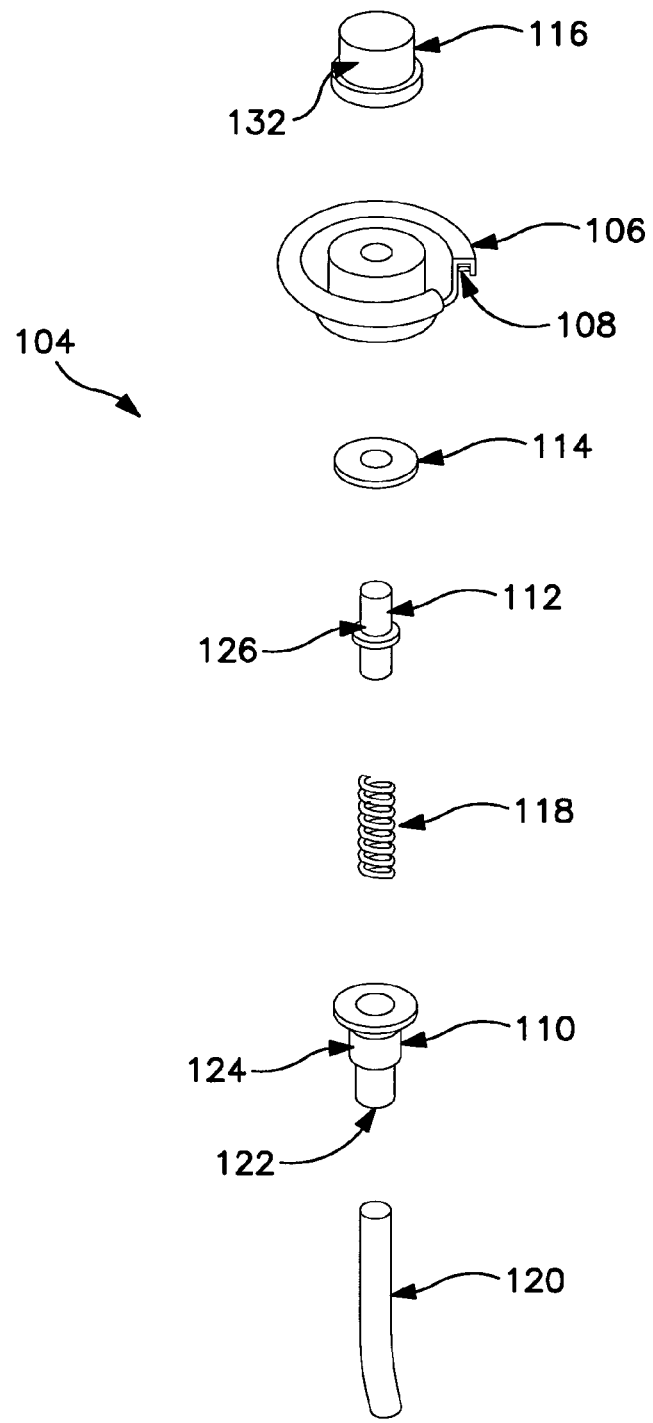
FIG. 3 is an exploded view of a conventional aerosol valve assembly and actuator cap.

As shown in FIG. 2, an aerosol dispenser assembly according to the invention generally comprises a container 2 with a valve assembly 4 disposed in the top thereof for selectively dispensing a liquid product from the container 2.

Figure 1:
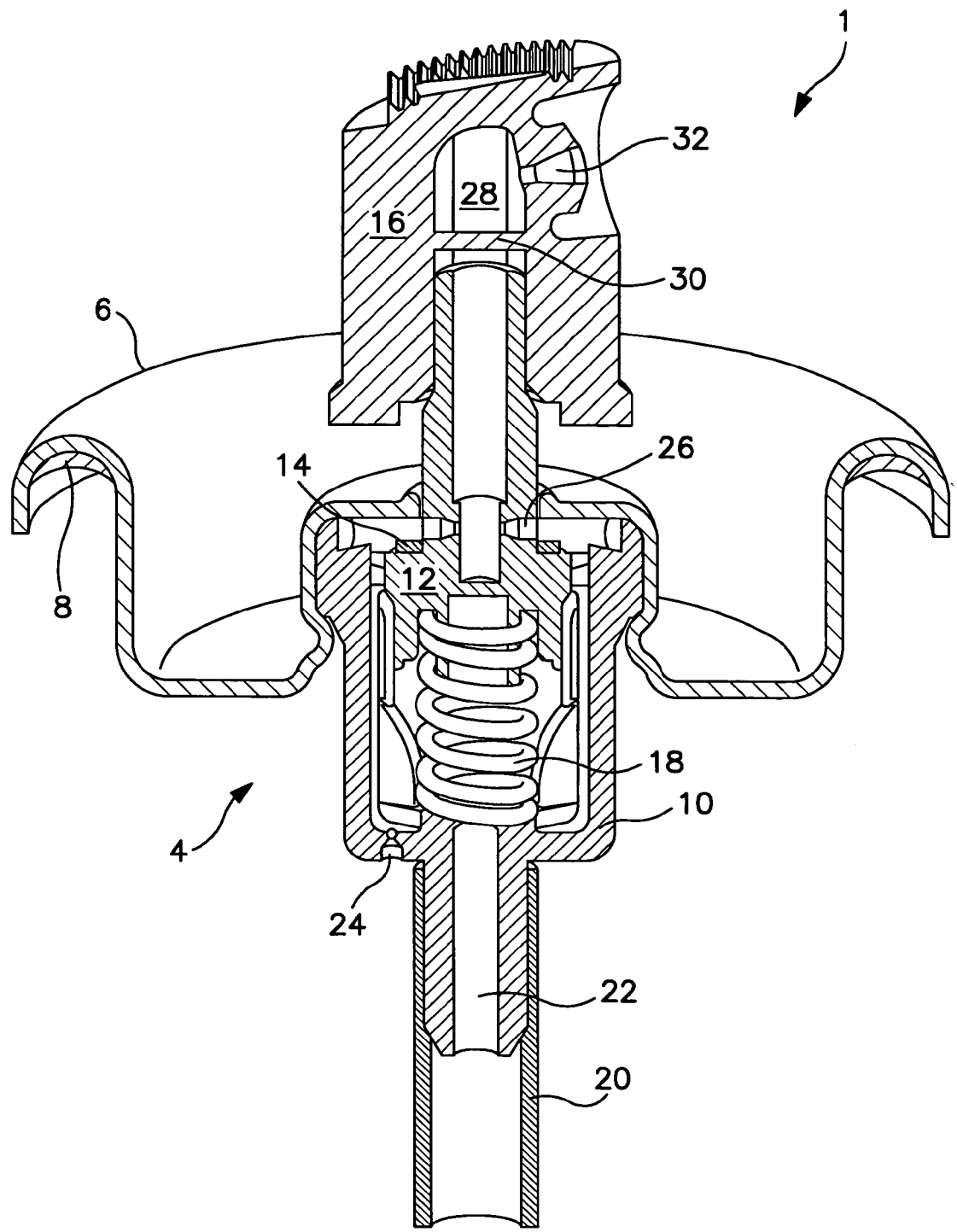
FIG. 1 is a cross-sectional perspective view of a first embodiment of a valve useful in practicing the present invention.

With reference to FIG. 1, the valve assembly 4 further comprises a mounting cup 6, a mounting gasket 8, a valve body 10, a valve stem 12, a stem gasket 14, an actuator cap 16, and a return spring 18. The actuator cap 16 defines an exit path 28 and an actuator orifice 32. The valve stem 12, stem gasket 14, and return spring 18 are disposed within the valve body 10 and are movable relative to the valve body 10. The valve body 10 affixes to the underside of the mounting cup 6, such that the valve stem 12 extends through, and projects outwardly from, the mounting cup 6. The actuator cap 16 fits onto the outwardly projecting portion of the valve stem 12, and a dip tube 20 attaches to the lower portion of the valve body 10. The whole valve assembly 4 is sealed to the container 2 by the mounting gasket 8.

While the actuator cap 16 is shown in FIG. 1 as being a simple push-button actuator, it will be understood that any suitable actuator may be used, such as, for example, an actuator button with an integral overcap.

In operation, when the actuator cap 16 of the dispenser 1 is depressed, it forces the valve stem 12 to move downward, opening the seal between the stem gasket and stem orifice(s) and thereby forming a flow path from the contents of the container to the outside environment. The propellant forces the liquid product up the dip tube 20 and into the valve body 10 via body orifice 22. In the valve body 10, the liquid product is mixed with additional propellant supplied to the valve body 10 through a vapor tap 24. The vapor tap 24 helps to mix the liquid product and propellant in the valve body 10, to thereby break up the product into smaller particles suitable to be dispensed. From the valve body 10, the liquid product is propelled through at least one stem orifice 26, out the valve stem 12, and through an exit path 28 formed in the actuator cap 16. As shown in FIG. 1, a pair of stem orifices 26 may be used. However, only one stem orifice is required. An agitating/mixing component is provided in the exit path to further mix or agitate the product. The agitating/mixing component may be any suitable component such as, but not limited to, a spin chamber, a breakup bar and/or a stem tortuosity which is bent with a breakup geometry. The breakup bar is a preferred agitating/mixing component. In a preferred embodiment, a breakup bar 30 is provided in the exit path, such that the product is forced to diverge around the breakup bar 30, thereby inducing turbulence in the flow of the product, further reducing the particle size of the product. The product is then expelled from the actuator cap 16 through an actuator orifice 32, which disperses the product and produces a desired spray pattern. In one variation of the dispenser assembly, instead of a breakup bar as shown in FIG. 1, the dispenser assembly might employ a pair of breakup plates positioned in or below the exit path 28.

Several valve components are known to affect the dispensed ratio of liquid product to propellant, these include the vapor tap, the stem orifice, the body orifice, and the inner diameter of the dip tube. In general, decreasing the size of the vapor tap has the effect of creating a leaner mixture (lower propellant to liquid ratio), reducing the amount of retention, but increasing the particle size and spray rate of the dispensed product. Conversely, decreasing the size of the stem orifice, body orifice, and/or dip tube inner diameter generally decreases both the spray rate and the particle size, and potentially increases the amount of product retention.

Based on the foregoing experimentation and analysis and as discussed hereafter, certain combinations of propellant type, can pressure, and valve orifice dimensions, produce a dispenser assembly that comprises at most 25%, more preferably 20%, by weight of a hydrocarbon propellant has a high quality spray, and thus product performance better than the prior art dispenser assemblies.

Additionally, the aerosol product dispenser assembly of FIGS. 1 and 2 is capable of satisfactorily dispensing an aqueous, two-phase, oil-out emulsion comprising at most 25% by weight of a hydrocarbon propellant and containing 5-25% of a water-soluble polyol with odor eliminating activity, when the diameter of the vapor tap 24 is between about 0.003" (0.076 mm) to about 0.020" (0.508 mm), more preferably from about 0.013" (0.330 mm) and about 0.019" (0.483 mm) for propellant contents in the 20-25% range and of about 0.003" (0.076 mm) to about 0.013" (0.330 mm) range for dispensing in the 15-20% propellant range. The diameter of the stem orifice 26 is between about 0.020" (0.508 mm) and about 0.030" (0.762 mm) when a single stem orifice is used (between about 0.014" (0.356 mm) and about 0.025" (0.635 mm) when a pair of stem orifices are used), the diameter of the body orifice is between about 0.008" (0.203 mm) and about 0.062" (1.575 mm), more preferably from about 0.050" (1.270 mm) and about 0.062" (1.575 mm) for propellant contents in the 20-25% propellant range and about 0.008" (0.203 mm)-about 0.050" (1.270 mm) for propellant contents in the 15-20% range, and the inner diameter of the dip tube is between about 0.040" (1.016 mm) and about 0.060" (1.524 mm).

Thus, any of the above described valve components, propellant types, propellant pressures, and valve orifice dimensions, may be used in combination to provide a dispenser assembly according to the invention.

In one currently preferred embodiment of the invention, the aerosol dispenser assembly 1 uses an A-Series propellant having a propellant pressure of about 57 psig (4.083 atm) (i.e., A-57 propellant) to dispense the liquid product from the container 2. In this embodiment, the container is initially pressurized to a can pressure of about 70 psig (4.763 atm) to about 80 psig (5.444 atm). The diameter of the vapor tap 24 in this embodiment is about 0.016" (0.406 mm). Two stem orifices 26 may be used, each having a diameter of about 0.024" (0.610 mm). The diameter of the body orifice is about 0.050" (1.270 mm), and the inner diameter of the dip tube is about 0.060" (1.524 mm). Furthermore, a breakup bar 30 is positioned in the exit path 28 of the actuator 16 in order to further reduce the particle size of the dispensed product.

Another preferred embodiment of the dispenser assembly 1 employs a single stem orifice 26. In this embodiment, the dispenser assembly 1 also uses the A-57 propellant and a can pressure of about 70 psig (4.763 atm) to about 80 psig (5.444 atm) to dispense the liquid product from the container 2. The diameter of the vapor tap is about 0.016" (0.406 mm), the diameter of the single stem orifice is about 0.025" (0.635 mm), the diameter of the body orifice is about 0.062" (1.575 mm), and the inner diameter of the dip tube is about 0.060" (1.524 mm). This embodiment also employs a breakup bar positioned in the exit path of the actuator to further reduce the particle size of the dispensed product.

These preferred embodiments of the dispenser assembly are capable of dispensing the liquid product contained within the container as a mist having an average particle size of less than or equal to 45 μm (0.0018"), over at least 75% of the life of the dispenser assembly. Because the dispensed mist has such a small particle size, the particles are more easily dispersed in the air and less fallout is experienced than with higher particle size producing assemblies containing limited propellant amounts of 25% propellant or less. This reduction in the amount of fallout increases the dispenser assembly's odor eliminating (removal) efficacy and helps to prevent undesirable residue of the liquid product from settling on flat surfaces, such as, countertops, tables, or floors. Additionally, the spray rate is preferably in a range from about 0.5 g per s to about 2.5 g per s for at least 75% of the life of the dispensing assembly.

While the preferred particle size and spray rate is described above and hereafter in test examples, particle size and spray rate can vary from dispenser to dispenser and due to various conditional variations such as, but not limited to, temperature, humidity and/or the like.

The spray rate 200 g per s and particle size 200 D(V,0.5) are late in life product performance measurements preferably collected at about 50-75% of the life of the product. Because the spray rate and particle size measurements consume product in their determination, the process of collecting two spray rate and two particle size measurements results in a decrease in the weight of the product that depends on the spray rate of the product. The value held constant to make the measurements is that there is close to 45% of the initial fill amount of product in the sample when the measurement process begins. This choice of initial level before late in life measurement allows the measurement to be suitably collected for a 260 gram fill weight in an 80 gram package for spray rates up to 2.5 g/sec, without running out of dispensable product in the process.

Moreover, these preferred embodiments of the dispenser assembly are capable of dispensing over 95% by weight of the liquid product from the container, i.e., leaving less than 5% product retention, and more preferably 98% by weight of the liquid product from the container, i.e., having less than 2% product retention. It is important that substantially all of the product can be dispensed to ensure that product label claims will be met. Also, by minimizing the amount of product retained in the container at the end of the life of the dispenser assembly, less liquid product is wasted. This is important from a consumer satisfaction standpoint, since consumers tend to be more satisfied with a dispenser assembly when substantially all of the liquid product can be dispensed.

Additional embodiments of the composition, valve, actuator overcap and spray performance parameters are described in the following examples. The examples are meant to be illustrative and not to be limiting.

EXAMPLES

Composition

| Label/ Composition No. | C1 | C2 | C3 | C4 | Comparative C5(B-40) C6(A-57) | Comparative C7 |
|---|---|---|---|---|---|---|
| Water (Deionized) | 72.5 | 67.4 | 34.1 | 34.8 | 15.0 | 0 |
| Ethanol (SDA 40B) | 0 | 0 | 34.5 | 38.4 | 62.4 | 63.9 |
| TEG (98%) | 6.1 | 6.1 | 6.1 | 6.1 | 6.1 | 6.1 |
| Emulsifier (Sorbitan Monooleate) | 1.4 | 0.81 | 0.61 | 0 | 0 | 0 |
| Fragrance (Various) (Optional) | 0.15 | 0.15 | 0.15 | 0.15 | 0.15 | 0.15 |
| Corrosion Inhibitor (Mono-Sodium Phosphate) | 0 | 0.35 | 0.07 | 0.32* | 0.2% (Sodium Benzoate) | 0 |
| pH Adjustor | 0 | 0.39 ($Na_2CO_3$) | 0.05 (NaOH) | 0 | 0.1% (Triethan-olamine) | 0 |
| Surface Disinfectant | 0 | 0 | 0 | 0.20** | 0 | 0 |
| Propellant | 20.0 (B52) | 24.96 (A57) | 24.57 (A57) | 20.0 (A57) | 16.0 (B40, A57) | 30.0 (B52) |
| Total VOC Content | 20 | 25.0 | 59.1 | 58.4 | 78.4 | 93.9 |

*Blend of $K_2NO_3$(0.12%) + $K_2HPO_4$ (0.02%) + $KH_2PO_4$(0.18%)
**Onyxide 3300, or alkyl dimethylbenzylammonium saccharinate Examples C1, C2, C3, and C4 form oil-out emulsions when shaken. Formation of an oil-out emulsion is critical to maintaining good spray performance.

pH=~8.5-9.5 for aqueous and/or hydroalcoholic portion.

Examples C5, C6, and C7 are single phase systems. No shaking is required and no two-phase emulsion is present.

Propellant content in the examples has a maximum level of 25%.

Ethanol content in examples C1, C2, C3, and C4 has a maximum level of 38.4%. In the comparative examples C5, C6, and C7, the contents of the composition dissolve in one another and form a single phase product. The presence of solvent (ethanol) is essential to the formation of the single phase liquid. However, ethanol increases the VOC content and, depending on the amount of ethanol present, can result in a composition having a high VOC content, such as shown for example by composition C7 which contains ethanol and no water. In order to reduce the VOC content of the composition, a portion or all of the ethanol content of the composition may be replaced with water, such as shown for example by compositions C1-C6. Since water is not classified as a VOC, the overall VOC content of the product is reduced when water is present in the composition. In examples C5 and C6 the ethanol content is sufficient to completely dissolve the added water. In example C3 and C4, the water content to too great and a two-phase system results. The hydroalcoholic mixture forms a two-phase oil-out emulsion when shaken, the stability of the so-formed emulsion is enhanced by the presence of the surfactant (in example C3).

The following two tables summarize suitable valves and overcaps, which when used with the respective formulas set forth above, produce the spray performance parameters reported in the third following table.

Valve

| Label/ Example | V1 | V2/V3 | V4 | V5/V6 | V7 |
|---|---|---|---|---|---|
| Vapor Tap | 0.005" | 0.016" | 0.016" | 0.013" | 0.020" |
| Body Orifice | 0.013" | 0.050" | 0.050" | 0.050" | 0.050" |
| Dip Tube Inner Diameter | 0.060" | 0.060" | 0.050" | 0.050" | 0.060" |
| Stem Orifice | 4 × 0.024" | 2 × 0.024" | 2 × 0.020" | 2 × 0.020" | 2 × 0.020" |
| Supplier | Precision Valve Corp. | Precision Valve Corp. | Precision Valve Corp. | Precision Valve Company | Precision Valve Company |

Actuator Overcap

| Label/ Example | AO1 | AO2/AO3 | AO4 | AO5/AO6 | AO7 |
|---|---|---|---|---|---|
| Form | 2 Piece Mechanical Break-up Button | Actuator Overcap | 2 Piece Mechanical Break-up Button | 2 Piece Mechanical Break-up Button | Actuator Overcap |
| Stem Tortuosity | Bent w/ Breakup Geometry | Straight Tubular | Bent w/ Breakup Geometry | Bent w/ Breakup Geometry | Straight Tubular |
| Spin Chamber | yes | no | Yes | yes | no |
| Breakup Bar | no | yes | No | no | no |
| Exit Orifice Diameter | 0.018" | 0.021" | 0.016" | 0.020" | 0.021" |

Spray Performance Parameters

| Label/ Example | SP1 | SP2 | SP3 | SP4 | SP5/SP6 | SP7 |
|---|---|---|---|---|---|---|
| Container Volume/ml | 359.5 | 359.5 | 359.5 | 554.7 | 359.5 | 472.7 |
| Fill Weight/g | 259.7 | 259.7 | 259.7 | 346.6 | 259.7 | 296.7 |
| Initial Spray Rate/g per s | 0.61 | 1.35 | 1.34 | 0.82 | 1.01 | 1.20 |
| Initial Particle Size D(V, 0.5)/micron | 41 | 37 | 40 | 39 | 58 | 33 |
| Spray Rate 200/g per s | 0.62 | 1.17 | 1.20 | 0.67 | 0.90 | 0.86 |
| Particle Size 200 D(V, 0.5)/micron | 43 | 38 | 42 | 31 | 61 | 41 |
| Retention % | 2 | <2 | <2 | <2 | <2 | <2 |

The valve and overcap combination for standard Package Revealed in V1 and A01 can alternatively be used for Examples C1 and C2 with similar performance results. Valve V7 for composition C7 is also available from Summit Packaging Systems (with body orifice=0.062", stem orifice=1× 0.025", dip tube ID=0.060", and vapor tap=0.020").

The compositions of the invention provide the following advantages:
  (1) Odor Elimination
  (2) A Fine Mist
  (3) Adequate Spray Rate
  (4) Low Retention
  (5) Lack of Can Corrosion
  (6) Low Manufacturing Cost
  (7) Absence of Toxicity or other Deleterious Effects The above examples were tested using predetermined test procedures. The following is an overview of the conditions and parameters of the test procedures used to measure conditions and results, including spray rate, particle size and retention.

Spray performance was evaluated at ambient indoor conditions: ~70° F. and ordinary humidity. Samples were stored at ambient indoor conditions for at least 24 hours before tests.

Spray rates were determined through weight change during a 10 second spray, are reported as grams per second, and are averaged over two sprays during the first 40 seconds of sample life. The actuator is completely depressed during the measurement. The can is shaken appropriately before spraying, allowing up to 2-4 seconds between shaking and spraying.

Spray rate 200 were collected after spraying the sample down to 200g (formula+package) and are averaged over two measurements.

Particle size is mass median diameter, D(V,0.5), reported in microns (micrometers, μm), as reported from Malvern® laser diffraction particle size analyzer equipped with a 300 mm lens. Aerosols were sprayed with the spray tip 18" from the probe beam. A cutoff was applied at 301.7 μm to eliminate ghost peaks caused by "beam steering". Spray times for particle size measurements were between 5 and 10 seconds, depending on the obscuration of the spray. Results were averaged over two measurements collected during the first 40 seconds of sample life. Samples were appropriately shaken before measurements were taken, allowing up to 2-4 seconds between shaking and spraying.

Particle size 200 is D(V,0.5), determined from Malvern®, and was collected on samples that were sprayed down to 200 grams (formula+package) and averaged over at least two measurements. Aerosols were sprayed with the spray tip 18" from the probe beam. Typically, particle size 200 and spray rate 200 measurements were alternated until two of each were completed.

Spray-down was accomplished by spraying cans for 10 second intervals once per hour, usually for a maximum of 6 sprays per day. This process tended to deplete the can pressure, which was regained on standing for 24 hours or so, depending on the amount of spray-down. Other critical measurements, such as particle size and spray rate were not measured within 24 hours of substantial spray down (3 or more ten second sprays).

Product retention is the weight of material remaining in the aerosol after complete discharge of the propellant through the spray-down procedure. The weight of retained product was determined by the difference in the final weight of the fully discharged package (when internal pressure equals ambient pressure) minus the weight of the package following opening the container and rinsing the remaining contents away with acetone (and drying). Product retention may be reported as grams retained or percent retained.

The procedures utilized to measure spray rate, particle size and retention are the same as described above throughout the description and claims.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments described herein.

It is claimed:

1. An odor eliminating composition for treating air for dispensing as an aerosol composition comprising:

a dispensing container including a spray head in combination with said composition for dispensing said composition from said container, wherein said composition based on 100 wt. %, comprises 5 wt. % to about 25 wt. % of at least one polyol having a molecular weight of about 250 grams/mole or less;

from about 0.4 wt. % to about 4 wt. % emulsifier when no solvent is present in the composition;

from about 10 wt. % to about 25 wt. % non-halogenated hydrocarbon propellant;

from about 20 wt. % to about 90 wt. % water;

from 0 wt. % to about 60 wt. % of a solvent which is one or more of a low molecular weight alcohol or acetone; and optionally, one or more components selected from the group consisting of fragrances, corrosion inhibitors, pH adjustors, antimicrobials, and preservatives;

wherein when said solvent is present in said composition, said solvent is present in an amount of about 25 to about 45 wt. % and is sufficient in amount to allow formation of an emulsion in absence of said emulsifier, said emulsifier can then be present in an amount of from 0 to about 4 wt. %; and wherein said composition is a two-phase oil-out emulsion and said spray head is adapted so that upon said composition being dispensed from said spray head of said dispensing container, said composition has an average particle size of less than or equal to 45 μm over at least 75% of a life of said composition and a spray rate in a range from about 0.5 g/sec to about 2.5 g/sec over at least 75% of said life of said composition.

2. The composition for treating air according to claim 1, wherein the propellant is present in an amount of 20 wt. % or less.

3. The composition for treating air according to claim 1, wherein the solvent is present in a range of about 30 to about 40 wt. %.

4. The composition for treating air according to claim 1, wherein no solvent is present.

5. The composition for treating air according to claim 1, wherein said emulsifier is sorbitan monooleate.

6. The composition for treating air according to claim 1, wherein a corrosion inhibitor is present and said corrosion inhibitor is monosodium phosphate.

7. The composition for treating air according to claim 1, wherein the polyol is one or more of a monoalkylene glycol, dialkylene glycol, trialkylene glycol or glycerol.

8. The composition for treating air according to claim 1, wherein the polyol is triethylene glycol.

9. The composition for treating air according to claim 1, wherein the at least one polyol is triethylene glycol and propylene glycol.

10. The composition for treating air according to claim 1, wherein the composition has a pH in a range of about 8 to about 10.

11. An odor eliminating composition for treating air for dispensing as an aerosol composition comprising:

a dispensing container including a spray head in combination with said composition for dispensing said composition from said container, wherein said composition based on 100 wt. %, comprises 5 wt. % to about 25 wt. % of at least one polyol having a molecular weight of about 250 grams/mole or less;

from about 0.4 wt. % to about 4 wt. % emulsifier when no solvent is present in the composition;

from about 10 wt. % to 20 wt. % non-halogenated hydrocarbon propellant;

from about 20 wt. % to about 90 wt. % water;

and optionally, one or more components selected from the group consisting of fragrances, corrosion inhibitors, pH adjustors, antimicrobials, and preservatives; and wherein said composition is a two-phase oil-out emulsion and said spray head is adapted so that upon said composition being dispensed from said spray head of said dispensing container, said composition has an average particle size of less than or equal to 45 μm over at least 75% of a life of said composition and a spray rate in a range from about 0.5 g/sec to about 2.5 g/sec over at least 75% of said life of said composition; and wherein no solvent is present.

12. An odor eliminating composition for treating air for dispensing as an aerosol composition comprising:

a dispensing container including a spray head in combination with said composition for dispensing said composition from said container, wherein said composition based on 100 wt. %, comprises 5 wt. % to about 25 wt. % of at least one polyol having a molecular weight of about 250 grams/mole or less;

from about 0.4 wt. % to about 4 wt. % emulsifier when no solvent is present in the composition;

from about 10 wt. % to about 25 wt. % non-halogenated hydrocarbon propellant;

from about 20 wt. % to about 90 wt. % water;

from 0 wt. % to about 60 wt. % ethanol; and optionally, one or more components selected from the group consisting of fragrances, corrosion inhibitors, pH adjustors, antimicrobials, and preservatives;

wherein when said ethanol is present in said composition, said ethanol is present in an amount of about 25 to about 45 wt. % and is sufficient in amount to allow formation of an emulsion in absence of said emulsifier, said emulsifier can then be present in an amount of from 0 to about 4 wt. %; and wherein said composition is a two-phase oil-out emulsion and said spray head is adapted so that upon said composition being dispensed from said spray head of said dispensing container, said composition has an average particle size of less than or equal to 45 μm over at least 75% of a life of said composition and a spray rate in a range from about 0.5 g/sec to about 2.5 g/sec over at least 75% of said life of said composition.

13. The composition for treating air according to claim 12, wherein said composition comprises 35% or less ethanol.

* * * * *